United States Patent [19]
Aizawa et al.

[11] Patent Number: 5,098,380
[45] Date of Patent: Mar. 24, 1992

[54] METHOD OF AND APPARATUS FOR DETECTING AN OCCLUSION OF LIQUID TRANSFUSION TUBE

[75] Inventors: Takeshi Aizawa; Akira Fujitani; Tetsuya Miyatake; Kazumi Yokoyama; Shigeru Tanaka, all of Tokyo, Japan

[73] Assignee: Nikkiso Co., Ltd., Tokyo, Japan

[21] Appl. No.: 330,473

[22] Filed: Mar. 30, 1989

[30] Foreign Application Priority Data

Mar. 30, 1988 [JP] Japan .................................. 63-74571

[51] Int. Cl.$^5$ ............................................. A61M 31/00
[52] U.S. Cl. ..................................... 604/67; 604/246; 128/DIG. 13
[58] Field of Search .................... 604/65, 67, 245, 246; 128/DIG. 12, DIG. 13

[56] References Cited

U.S. PATENT DOCUMENTS

| 4,029,094 | 6/1977 | Winicki | 128/DIG. 13 |
| 4,373,525 | 2/1983 | Kobayashi | 128/DIG. 13 |
| 4,526,574 | 7/1985 | Pekkarinen | 128/DIG. 13 |
| 4,690,673 | 9/1987 | Bloomquist | 128/DIG. 13 |
| 4,846,792 | 7/1989 | Bobo, Jr. et al. | 128/DIG. 13 |

Primary Examiner—Lee S. Cohen
Assistant Examiner—J. P. Lacyk
Attorney, Agent, or Firm—Young & Thompson

[57] ABSTRACT

There is disclosed an apparatus for detecting an occlusion of a liquid transfusion tube in which a pump section is provided in a liquid transfusion tube for connecting an infusion liquid container with a body infusion element. An occlusion of the liquid transfusion tube is detected according to an amount of displacement of the liquid transfusion tube displaceable under a pressure of a liquid transfused to the liquid transfusion tube by an operation of the pump section.

4 Claims, 4 Drawing Sheets

TUBE EXPANSION BY APPLYING A PRESSURE OF 0.8 Kg/cm²

SEQUENTIAL CHANGE OF TUBE IN THE STATE OF NO PRESSURE

RELATION BETWEEN FLUX DENSITY AND
OUTPUT VOLTAGE OF HALL SENSOR

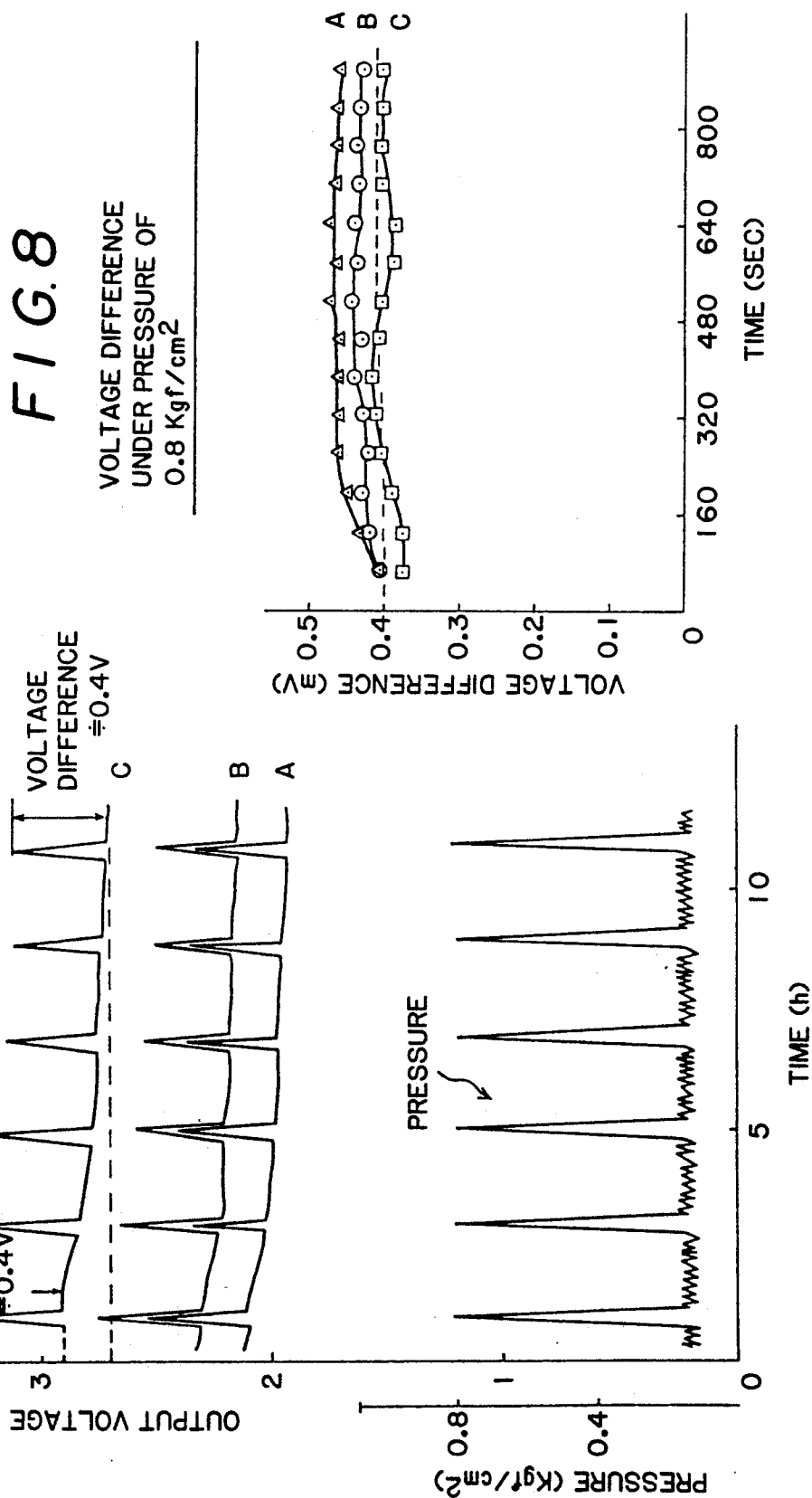

METHOD OF AND APPARATUS FOR DETECTING AN OCCLUSION OF LIQUID TRANSFUSION TUBE

FIELD OF THE INVENTION

This invention relates to a method of and an apparatus for detecting an occlusion of a liquid transfusion tube, particularly in a liquid transfusion pump in accordance with an amount of variation of displacement of the liquid transfusion tube displaceable under the pressure of the liquid transfused into the liquid transfusion tube.

BACKGROUND OF THE INVENTION

In general, a peristaltic finger pump is used as a liquid transfusion device for an automatic instillation device and is provided between an infusion liquid container such as a pharmaceutical liquid bottle and a body infusion member like an infusion needle as disclosed in the Japanese Laid-Open Patent Publication No. 58-165868. The pump of this type is so constructed that a predetermined quantity of a liquid is transfused by squeezing an elastic liquid transfusion tube in a liquid transfusing direction by movements of a plurality of the finger members. When a clamper and the like disposed in a liquid transfusion tube system to occlude a pharmaceutical liquid fail to open and thereby produce an occluded state for an extended period and a desired quantity of a liquid is not infused, or when a tip of an infusion needle is clogged so that a joint for the liquid transfusion tube is released and when an inner pressure of the liquid transfusion tube is elevated upon release of the clogging with an accidental infusion of the pharmacheutical liquid, which causes trouble. In particular, premature babies and patients in critical condition are subjected to great danger.

Therefore, it has been required to detect such an occlusion of a liquid transfusion tube quickly for prevention of an occurrence of any trouble. There has been a particular apparatus for detecting an occlusion of the liquid transfusion tube to detect an expansion of the transfusion tube due to a variation of a liquid pressure in the liquid transfusion tube by a strain gauge and the like to give an alarm.

However, according to the conventional method of and apparatus for detecting an occlusion of the liquid transfusion tube, the liquid transfusion tube to be detected is required to have an expansion sufficient for detection by a strain guage and the like when an inner pressure is elevated by an occlusion and also to have a constant expansion rate for each liquid transfusion unit, notwithstanding there is no substantial expansion from the spontaneous state even when clogginhg has occurred and also that the conventional apparatus could not be used for the general purpose liquid transfusion unit receiving liquid transfusion tubes of different hardness according to the manufacturers.

The conventional liquid transfusion unit is an istillation liquid transfusion unit manufactured not for use with squeezing by a pump, and since this liquid transfusion unit is free of any squeezing portion for the pump, the structure is simple for mass-production in a single species with the reduced cost.

According to the present invention, when the liquid transfusion tube to be used for the general-purpose liquid transfusion unit is pressurized into a flat shape, the flat portion is sharply displaced against the variation of the liquid pressure in the liquid transfusion tube.

SUMMARY OF THE INVENTION

Therefore, an object of the present invention is to provide a method of an an apparatus for detecting an occlusion of a liquid transfusion tube, in which a liquid transfusion tube on the downstream side of a pump is inserted into an insertion portion in a flattened state and the flattened portion of this liquid transfusionn tube is pressed elastically by the clamping portion on the pivoting members, a degree a displacement of the flattenned portion of the liquid transfusion tube is detected by the detector disposed on the pivoting members, thereby enabling to apply the method and apparatus to a general-purpose liquid transfusion tube.

To achieve the foregoing object according to the invention, there is provided an apparatus for detecting an occlusion of a liquid transfusion tube wherein a pump section is provided in a liquid transfusion tube for connecting an infusion liquid container with a body infusion element, so that an occlusion of said liquid transfusion tube is detected according to quantity of displacement of the liquid transfusion tube displacing under a pressure of the liquid transfused thereto by an operation of the pump section wherein there are provided an insertion portion for inserting the liquid transfusion tube on the downstream side of the pump section in a flattened state, a pair of pivoting members provided with a clamping portion at one end so as to elastically press a flattened part of the liquid transfusion tube according to movements of the pivoting members, a detector disposed between the pivoting members to detect quantity of displacement of a distance between the detecting members, a means for comparing a value of a detected signal output from the detector with a reference value, and an alarm for outputting a warning when a value of the detected signal exceeds over said reference value.

In the foregoing apparatus, the detectors to be disposed between the pivoting members may preferably be comprised of a hall sensor unit.

Further, pivoting members may preferably be formed of compression springs.

Moreover, in the method of detecting an occlusion of a liquid transfusion tube according to the present invention, a pump section is provided in a liquid transfusion tube for connecting an infusion liquid container with a body infusion element, an occlusion of said liquid transfusion tube is detected according to an amount of displacement of the liquid transfusion tube displacing under a pressure of the liquide transfused into the liquid transfusion tube by an operation of the pump section, wherein a liquid transfusion tube on the downstream side of the pump section is inserted into an insertion portion in a flattened state, the flattened portion of said liquid transfusion tube is elastically pressed at a clamping portion of the pivoting member, an amount of displacement between the pivoting members displaceable according to variation of an inner pressure in the liquid transfusion tube is detected by a detecting unit disposed between the pivoting members, a value detected by the detector is sequentially compared with a predetermined reference value and an alarm signal is output when the detected value exceeds the reference valve, thereby to stop an operation of the pump section.

Furthermore, against an elastically pressing operation to make a liquid transfusion tube at a clamping portion of a pivoting member in a flattened state, the pivoting member may preferably be operated to enlarge a space between the detectors disposed in a confronting relation.

BRIEF DESCRIPTION OF THE DRAWINGS

An apparatus for detecting an occlusion of a liquid transfusion tube according to the present invention is described hereinafter in detail in connection with a method of operating this apparatus and with reference to the accompanying drawings.

FIG. 7 is a waveform diagram showing a relation between an internal pressure of the liquid transfusion tube on account of an experiment of the liquid transfusion tube and the output voltage thereagainst; and FIG. 8 is a characteristic diagram showing sequential variations of a voltage difference with an internal pressure applied to the liquid transfusion tube by using the detecting apparatus according to the present invention.

PREFERRED EMBODIMENT OF THE INVENTION

Figure 1:
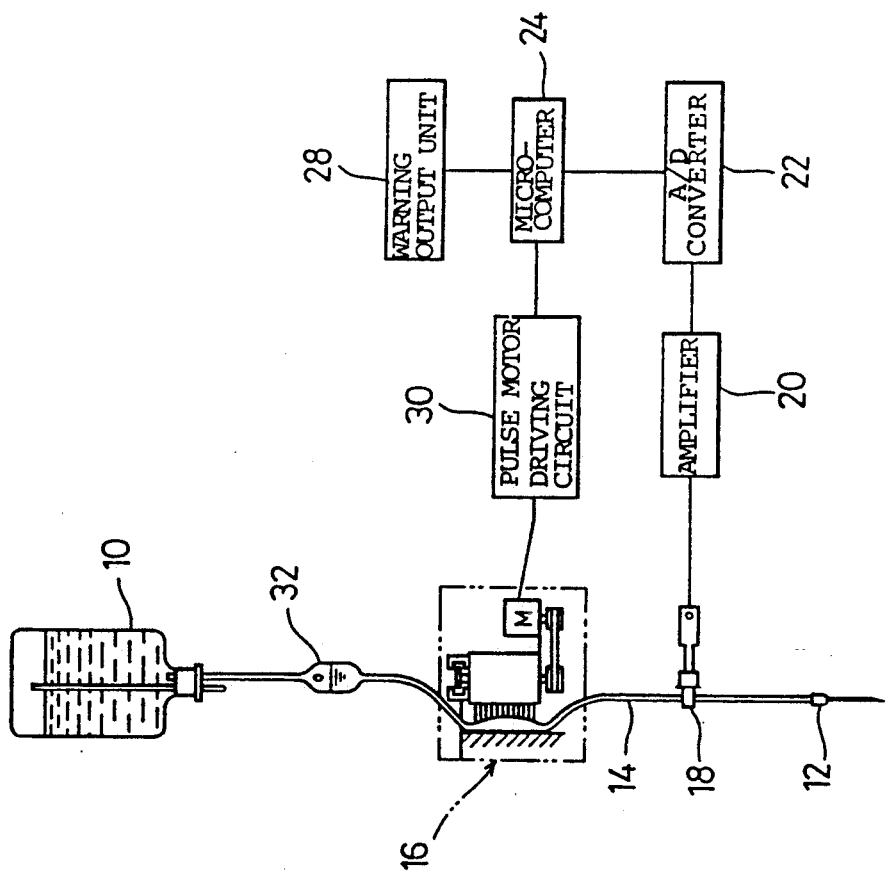
FIG. 1 is a pictorial view showing an embodiment descriptive of an apparatus for detecting an occlusion of a liquid transfusion tube incorporated into a liquid transfusion equipment according to the present invention.

In FIG. 1, a liquid transfusion equipment in accordance with this embodiment is essentially comprised of a liquid infusion container of a pharmaceutical bottle 10, a body infusion element or an infusion needle 12 and a liquid transfusion tube 14 connection thereof which provides a pump section or a peristaltic finger pump 16.

The pump section 16 at its downstream is provided with an occlusion detection means 18 according to the invention to which is connected an amplifier 20 for electrically receiving the detected signal for amplification. An amplified signal is converted by an A/D converter 22 for transmission into a microcomputer 24 in which an occlusion of the liquid transfusion tube is sequentially monitored by a comparator. When the detection value exceeds the reference value a warning signal is output through a warning output unit 28 while pulse motor driving circuit 30 actuating as a driving source of the pump unit 16 is stopped. Further, the reference numeral 32 represents an instillation sleeve.

Figure 2:
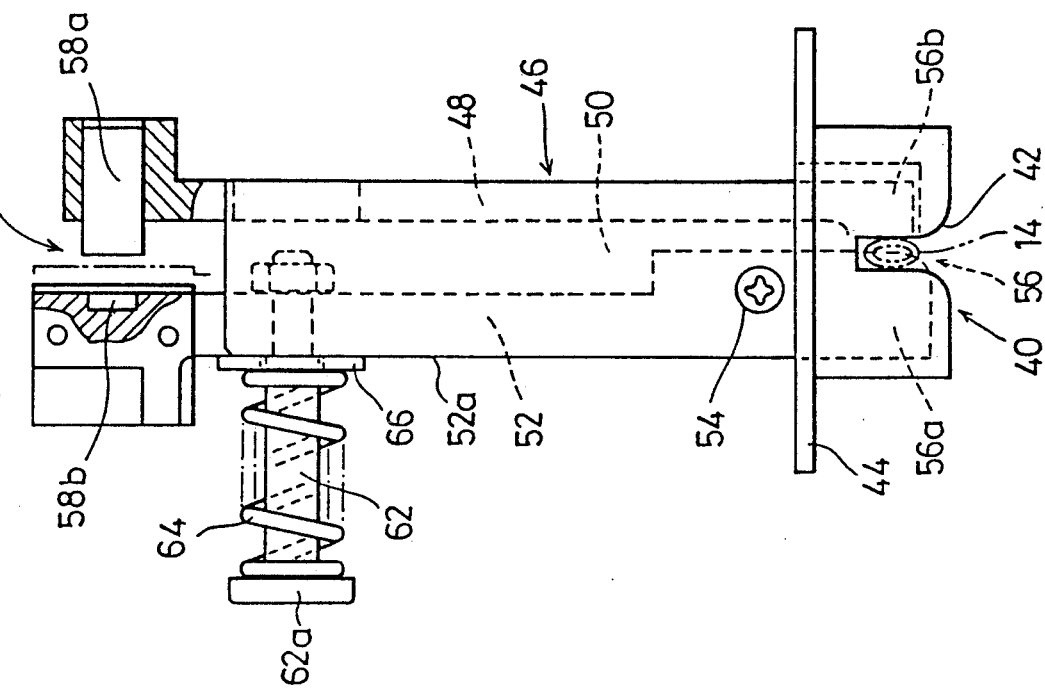
FIG. 2 is a partially sectioned front elevation showing an embodiment descriptive of the apparatus for detecting an occlusion of the liquid transfusion tube according to FIG. 1.

In FIG. 2, the reference 14 denotes a liquid transfusion tube for use in the general-purpose liquid transfusion unit, 40 stands for an insertion portion forming a rounded portion 42 for receiving a liquid transfusion tube in the flattened state. In the insertion portion 40 is provided a flange member 44 to be secured to a fixed member. Further, to the insertion portion 40 is integrally secured an arm 48 constituted by a pivoting member 46, while facing a groove 50 formed alongside of the arm 48 is provided an arm 52 with a pivot pin 54.

The pivoting member 46 forming a pair of the arms 48 and 52 provides at its one end clamping portions 56a and 56b to clamp the flattened portion of the liquid transfusion tube 14 for embracement under pressure.

Further, the clamping portions 56a and 56b extend into the inserting portion 40 for embracing the flattened portion for the liquid transfusion tube.

Moreover, the fixed arm 48 of the pivoting member 46 at its one end opposite to the clamping portion 56b is provided with a magnet 58a constituting the detector 58 while the pivoting arm 52 at its one end is provided with a hall sensor 58b facing the magnet 58a to actuate the detector 58 and to the hall sensor 58b is connected a lead wire (not shown) for withdrawing an electric signal. In the vicinity of the fixed hall sensor 58b of the pivoting arm 52, a headed pin 62 is buried.

Between a washer 66 freely mounted around the headed pin 62 and a head portion 62a of the headed pin 62 is interposed a compression spring 64 so that a washer 66 is brought into contact with the fixed arm 48 under energization of the compression spring 64 while a sensing terminal of the pivoting arm 52 is separated at maximum from the fixed arm 48.

Figure 3:
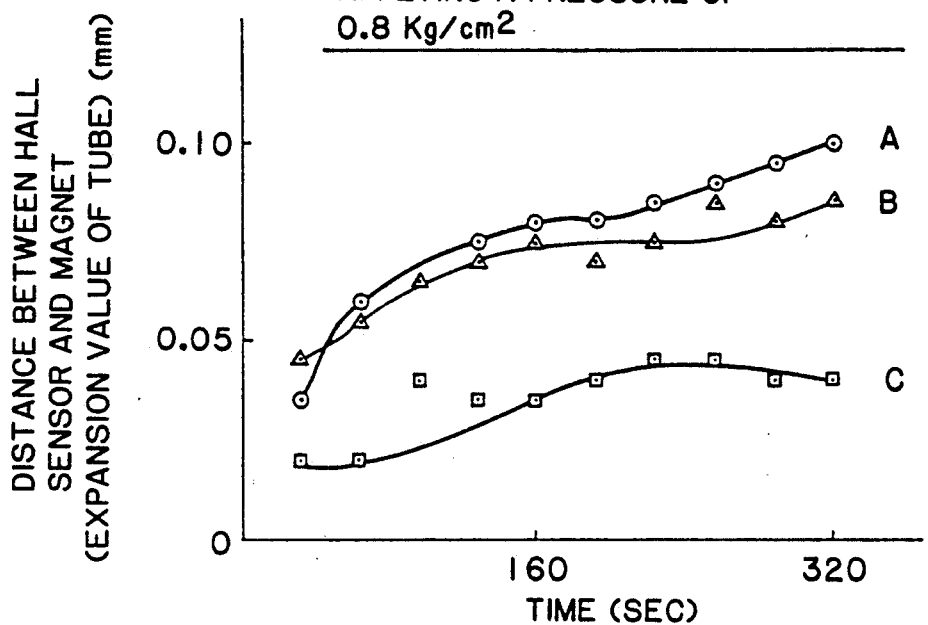
FIG. 3 is a characteristic diagram showing a sequential variation of an expansion value of the liquid transfusion tube to which a certain internal pressure is applied.
Figure 4:
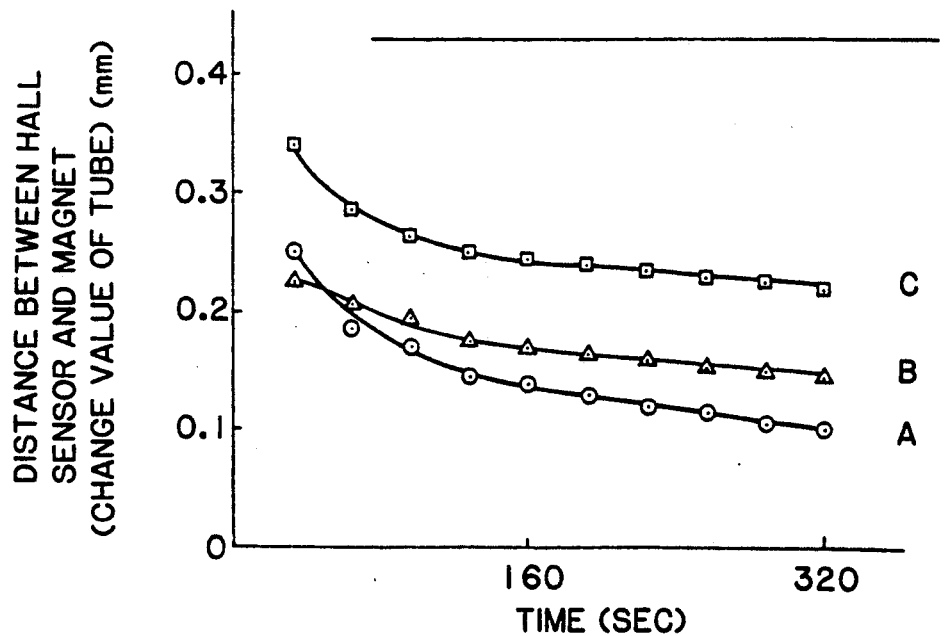
FIG. 4 is a characteristic diagram showing a sequential variation of the flattening value of the liquid transfusion tube when an external force is applied in the state free of an inner pressure.

The generally used liquid transfusion tubes made by the different manufacturers have been investigated to obtain characteristics thereof as shown in FIGS. 3 and 4. Namely, FIG. 3 is a characteristic diagram showing a sequential variation value under the internal pressure applied to the tube. The diagram shows the sequential variation of the expansion when the tube of each manufacturer is inserted respectively into the insertion portion of the occlusion detecting means for applying the internal pressure of 0.8 Kg/cm$^2$ to the tube thereby to identify the sequential variation of the expansion rate by means of the detector 58.

In the characteristic diagram, an expansion rate of the tube made by the manufacturer A after approximately five minutes is about 0.07 mm while an expansion rate of the manufacturer C is approximately 0.02 mm so that the difference in expansion rate between the A tube and the C tube is 0.05 mm at maximum.

In FIG. 4, a tube of each manufacturer is inserted respectively into the insertion portion 40 of an occlusion detecting equipment and the pressure under the compressing spring of the detecting means only is applied to the flattened portion of the tube to obtain a flattening rate of the tube as a sequential variation.

In the diagram, the flattening rate of the tube made by the manufacturer A about 5 minutes later is about 0.15 mm while the flattening rate of the manufacturer B is 0.08 mm leaving the difference between the A tube and the C tube as 0.07 mm at maximum.

Accordingly, it will be appreciated from the characteristic diagram that the flattening rate is sequentially changed with considerably irregular results in the tubes of the different manufacturers.

Figure 5:
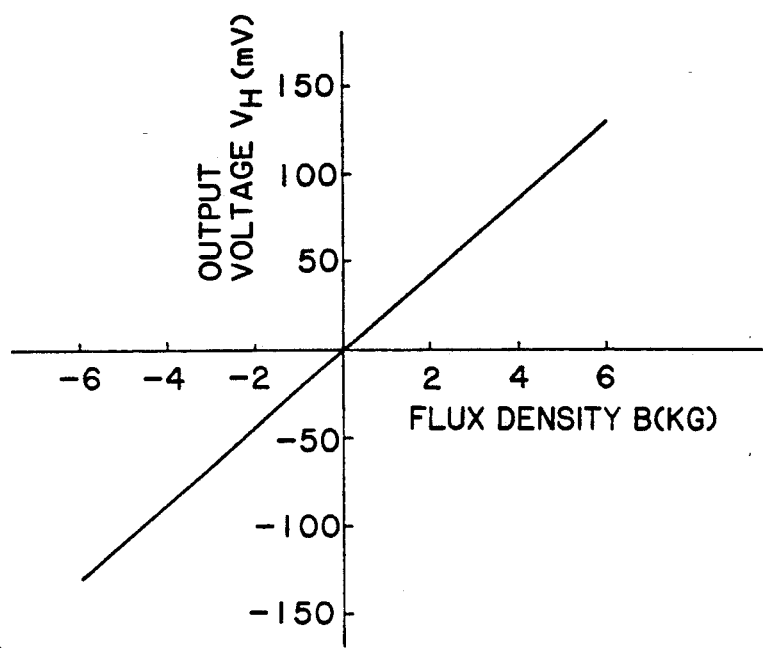
FIG. 5 is a characteristic diagram showing a relation between a magnetic flux density and an output voltage.

Further, in FIG. 5, the characteristic diagram of the flux density with the output voltage showing a hall sensor to be used in the detector has relatively a linear chacteristic in the relation of the flux density B (KG) with the output valtage $V_H$ (mV).

Figure 6:
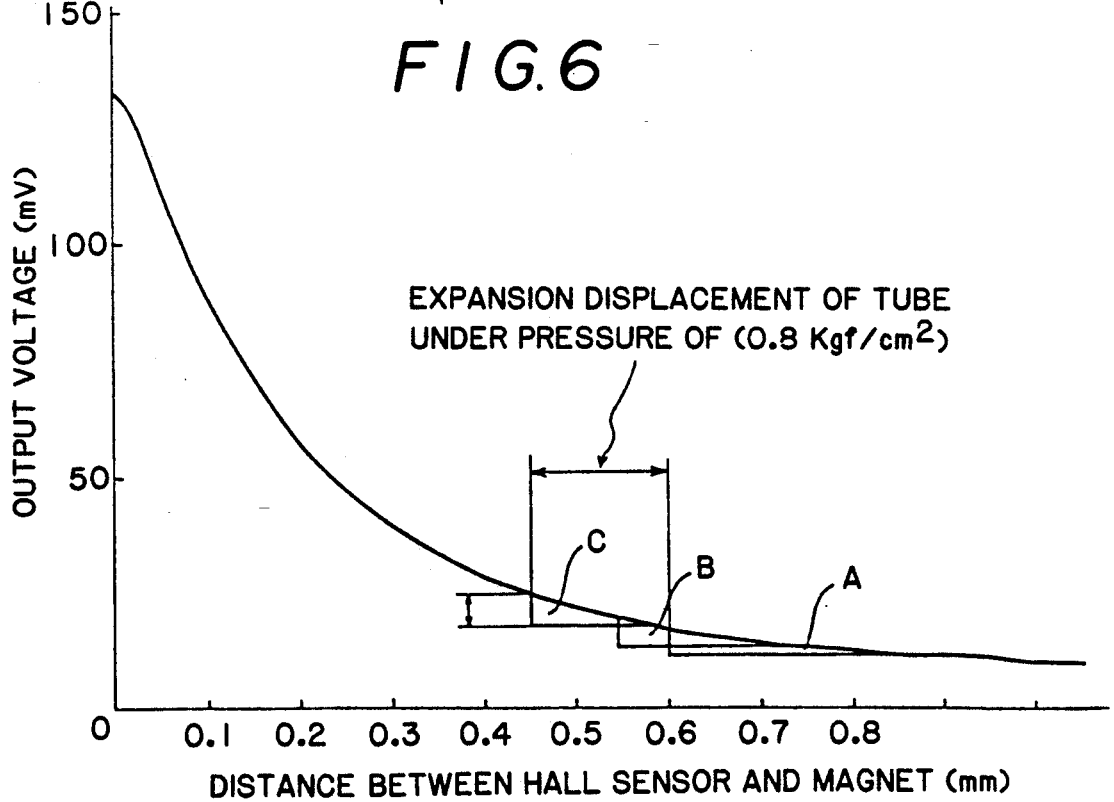
FIG. 6 is a characteristic diagram of a detector showing a relation of a distance between a hall sensor and a magnet with an output voltage.

Moreover, as obvious from FIG. 6 of the characteristic diagram, a relation of the space between the hall sensor and the magnet with the output voltage has an inversely proportional non-linear characteristic so that a space between the hole sensor 52 and the magnet 58 is determined to obtain a voltage variation substantially equivalent to the output voltage value against the irregular expansions (0.8 Kg F/cm$^2$) of the A tube, B tube and C tube respectively.

In FIG. 7, an internal pressure of 0.8 Kg F/cm$^2$ is applied to the tube as a pulse of the constant time to obtain a sequential variation of the output voltage so that in each tube approximatly 10 hours later the output voltage free of any pressure is decreased to approximately 0.2 V while when an internal pressure of 0.8 Kg F/cm$^2$ is applied, the difference in output voltage in each time is 0.4 V, for which reason despite of an elongated used of the occlusion pressure detecting apparatus according to the invention, the detecting signal in relation to the variation of the internal pressure may be obtained in constant.

Further, as apparent from characteristic diagram of FIG. 8, the tubes of the different manufacturers have the values of substantially no sequential variation in the voltage difference.

As hereinbefore fully described, according to the invention, the safety of the liquid transfusion pump using a general-purpose liquid transfusion unit may be considerably enchanced with the constant detecting effects even in use of various tubes of the different manufacturers, thus the liquid transfusion system with an enhanced safety may be realized at a reduced cost using the general-purpose liquid transfusion unit.

Suitable embodiment of the invention has been described to explain the invention, notwithstanding a variety of changes in design may be practicable without departing from the scope and spirit of the invention.

What is claimed is:

1. An apparatus for detecting an occlusion of a liquid transfusion tube by detecting an amount of displacement of the liquid transfusion tube, comprising an insertion portion for receiving the liquid transfusion tube in a flattened state, a pair of pivoting members connected to the insertion portion and provided with a clamping portion at one end so as to elastically press a flattened part of the liquid transfusion tube in accordance with movements of said pivoting members, a detector disposed between said pivoting members to detect an amount of displacement of a space between the detecting members and to output a signal representative thereof, a means for comparing the value of said signal output from the detector with a predetermined reference value and an alarm means for outputting a warning when said signal exceeds said reference value, wherein said insertion portion comprises a pair of opposed rounded surfaces defining a slot of predetermined width, whereby a liquid transfusion tube having an exterior diameter greater than said predetermined width is received in said slot in a flattened state.

2. An apparatus for detecting an occlusion of the liquid transfusion tube according to claim 1, wherein the detector disposed between said pivoting members comprise a hall sensor unit.

3. An apparatus for detecting an occlusion of the liquid transfusion tube according to claim 1, wherein said pivoting members further include compression springs attached thereto.

4. A method of detecting an occlusion of a liquid transfusion tube wherein an occlusion of said liquid transfusion tube is detected according to an amount of displacement of said liquid transfusion tube under a pressure of a liquid transfused to the liquid transfusion tube, comprising inserting a liquid transfusion tube on a downstream side of a peristaltic pump section of a transfusion device into an insertion portion of a pair of pivoting members in a flattened state, elastically pressing the flattened portion of said liquid transfusion tube at a clamping portion of the pivoting members, detecting an amount of displacement between the pivoting members using a detecting unit disposed between the pivoting members, sequentially comparing a value detected by the deteceing unit with a predetermined reference value and outputting an alarm signal when the detected value exceeds the reference value, wherein said insertion portion comprises a pair of opposed rounded surfaces defining a slot of predetermined width, whereby a liquid transfusion tube having an exterior diameter greater than said predetermined width is received in said slot in a flattened state.

* * * * *